United States Patent
Skluzacek

(10) Patent No.: US 11,712,538 B2
(45) Date of Patent: Aug. 1, 2023

(54) TRAUMATIC NIGHTMARE DETECTION AND INTERVENTION

(71) Applicant: NIGHTWARE, INC., Minneapolis, MN (US)

(72) Inventor: Tyler Skluzacek, Chicago, IL (US)

(73) Assignee: NIGHTWARE, INC., Minneapolis, MN (US)

( * ) Notice: Subject to any disclaimer, the term of this patent is extended or adjusted under 35 U.S.C. 154(b) by 0 days.

(21) Appl. No.: 17/948,561

(22) Filed: Sep. 20, 2022

(65) Prior Publication Data

US 2023/0038328 A1 Feb. 9, 2023

Related U.S. Application Data

(63) Continuation of application No. 16/994,818, filed on Aug. 17, 2020, now Pat. No. 11,471,644, which is a
(Continued)

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/0205* (2013.01); *A61B 5/165* (2013.01); *A61B 5/4815* (2013.01); *A61B 5/4836* (2013.01); *A61B 5/681* (2013.01); *A61B 5/024* (2013.01); *A61B 5/11* (2013.01); *A61B 2562/0219* (2013.01); *A61M 2021/0022* (2013.01); *A61M 2021/0027* (2013.01);
(Continued)

(58) Field of Classification Search
CPC .................................................... A61M 21/02

USPC .......................................................... 600/301
See application file for complete search history.

(56) References Cited

U.S. PATENT DOCUMENTS

| 10,765,831 B1 | 9/2020 | Skluzacek |
| 11,284,834 B1 | 3/2022 | Milbert et al. |
| (Continued) | | |

FOREIGN PATENT DOCUMENTS

WO 2010107788 9/2010

OTHER PUBLICATIONS

"U.S. Appl. No. 15/713,313, Non Final Office Action dated Aug. 2, 2019", 8 pgs.

(Continued)

*Primary Examiner* — Kesha Frisby
(74) *Attorney, Agent, or Firm* — Schwegman Lundberg & Woessner, P.A.

(57) ABSTRACT

The present disclosure, in one embodiment, is a computer-implemented method for the detection of and intervention in traumatic nightmares. In one embodiment, a user wears a watch wirelessly connected to a phone. The watch may include an accelerometer, gyroscope, and heartrate monitor. The application may monitor these sensors and intervene with haptic feedback if the application detects a traumatic nightmare. In one embodiment, the application may include a monitoring module that collects data from the watch's accelerometer, gyroscope, and heartrate sensors. The application may then estimate and record stress levels based on these sensors. The application may also include an intervention module that responds to high stress levels with haptic feedback that increases in intensity of previous efforts to intervene were unsuccessful.

20 Claims, 6 Drawing Sheets

Related U.S. Application Data continuation of application No. 15/713,313, filed on Sep. 22, 2017, now Pat. No. 10,765,831.

(60) Provisional application No. 62/398,908, filed on Sep. 23, 2016.

(51) Int. Cl.

| | |
|---|---|
| *A61B 5/0205* | (2006.01) |
| *A61B 5/16* | (2006.01) |
| *A61B 5/11* | (2006.01) |
| *A61M 21/00* | (2006.01) |
| *A61B 5/024* | (2006.01) |

(52) U.S. Cl.
CPC .............. *A61M 2021/0044* (2013.01); *A61M 2205/3303* (2013.01); *A61M 2230/06* (2013.01); *A61M 2230/63* (2013.01)

(56) References Cited

U.S. PATENT DOCUMENTS

| | | |
|---|---|---|
| 11,471,644 B2 | 10/2022 | Skluzacek |
| 2005/0154264 A1 | 7/2005 | Lecompte et al. |
| 2014/0245784 A1 | 9/2014 | Proud et al. |
| 2015/0031964 A1 | 1/2015 | Bly et al. |
| 2015/0087894 A1 | 3/2015 | Rink et al. |
| 2015/0169844 A1 | 6/2015 | Munafo et al. |
| 2016/0296157 A1 | 10/2016 | Girouard |
| 2017/0071551 A1 | 3/2017 | Jain et al. |
| 2017/0209053 A1 | 7/2017 | Pantelopoulos et al. |
| 2018/0116607 A1 | 5/2018 | Yu et al. |
| 2020/0376231 A1 | 12/2020 | Skluzacek |
| 2022/0346704 A1 | 11/2022 | Milbert et al. |

OTHER PUBLICATIONS

"U.S. Appl. No. 15/713,313, Response filed Nov. 4, 2019 to Non Final Office Action dated Aug. 2, 2019", 9 pgs.

"U.S. Appl. No. 15/713,313, Final Office Action dated Feb. 6, 2020", 9 pgs.

"U.S. Appl. No. 15/713,313, Response filed Apr. 6, 2020 to Final Office Action dated Feb. 6, 2020", 8 pgs.

"U.S. Appl. No. 15/713,313, Notice of Allowance dated May 6, 2020", 7 pgs.

"U.S. Appl. No. 16/405,193, Non Final Office Action dated Oct. 22, 2020", 26 pgs.

"U.S. Appl. No. 16/405,193, Response filed Jan. 19, 2021 to Non Final Office Action dated Oct. 22, 2020", 23 pgs.

"U.S. Appl. No. 16/405,193, Final Office Action dated Feb. 12, 2021", 34 pgs.

"U.S. Appl. No. 16/405,193, Response filed Jun. 11, 2021 to Final Office Action dated Feb. 12, 2021", 16 pages.

"U.S. Appl. No. 16/405,193, Non Final Office Action dated Jul. 6, 2021", 20 pgs.

"U.S. Appl. No. 16/405,193, Response filed Sep. 24, 2021 to Non Final Office Action dated Jul. 6, 2021", 12 pages.

"U.S. Appl. No. 16/994,818, Non Final Office Action dated Sep. 29, 2021", 10 pgs.

"U.S. Appl. No. 16/405,193, Notice of Allowance dated Nov. 19, 2021", 11 pgs.

"U.S. Appl. No. 16/405,193, Notice of Allowability dated Dec. 9, 2021", 2 pgs.

"U.S. Appl. No. 16/994,818, Response filed Feb. 22, 2022 to Non Final Office Action dated Sep. 29, 2021", 10 pgs.

"U.S. Appl. No. 16/994,818, Notice of Allowance dated Jun. 15, 2022", 7 pgs.

"U.S. Appl. No. 17/689,262, Preliminary Amendment filed Aug. 16, 2022", 8 pgs.

100 102 104 106 108

TRAUMATIC NIGHTMARE DETECTION AND INTERVENTION

CROSS-REFERENCE TO RELATED APPLICATIONS

This application is a continuation of U.S. patent application Ser. No. 16/994,818, filed Aug. 17, 2020, which is a continuation of U.S. patent application Ser. No. 15/713,313, filed Sep. 22, 2017, which claims the benefit of provisional patent application Ser. No. 62/398,908, filed Sep. 23, 2016, each of which is hereby incorporated herein by reference in its entirety.

BACKGROUND OF THE INVENTION

Field of the Invention

The present disclosure relates to nightmares, particularly the detection of and intervention in traumatic nightmares.

Discussion of the Background

The background description provided herein is for generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Nightmares are a condition that affects a substantial number of persons, and particularly concerning segments of the population that experience nightmares are adults who have post-traumatic stress disorder (PTSD). Military veterans, first responders, and crime victims may be particularly afflicted with nightmares because of traumatic experiences that have created PTSD. Traumatic nightmares can be so impactful that restful sleep is negatively affected, and fragmented, possibly at times rendering people unable to function normally in their daily lives.

Many researchers have attempted to solve for traumatic nightmares, generally involving complex solutions in clinical settings using prolonged exposure or similar treatments. Drawbacks to existing solutions include cost, complexity, side effects, and inability to eliminate the effects of nightmares.

Problems associated with PTSD are particularly acute in the community of military veterans who have returned from combat operations, where the effort needed to begin clinical treatment may be great. Moreover, issues of self-esteem with military veterans may prevent them from pursuing clinical treatment, thereby prolonging their condition.

A method that uses readily available and relatively low-cost technology to monitor the sleep cycle of a person who experiences nightmares to interrupt the sleep cycle sufficiently to prevent the full onset of the nightmare from occurring, would provide decided advantages.

BRIEF SUMMARY OF THE INVENTION

The following presents a simplified summary of one or more embodiments of the present disclosure to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, is a computer-implemented method for the detection of and intervention in traumatic nightmares. In one embodiment, a user wears a watch wirelessly connected to a phone. The watch may include an accelerometer, gyroscope, and heartrate monitor. The application may monitor these sensors and intervene with haptic feedback if the application detects a traumatic nightmare.

In one embodiment, the application may include a monitoring module. A user may tap the applications' start button to begin monitoring. The application may spend the next minute collecting data from the watch's accelerometer, gyroscope, and heartrate sensors. The application may average the sensor values over the previous minute. The application may compute an instantaneous stress magnitude for the previous minute. The application may compute an average stress magnitude by averaging the instantaneous stress magnitudes over the last five minutes. The application may record the average sensor values, instantaneous stress magnitude, and average stress magnitude locally and in the cloud.

In one embodiment, the application may include an intervention module. The module may receive a notification that the application recorded a sample. The module may determine whether it has collected at least 4,000 samples. If so, the module may determine if the module has intervened in the last five minutes. If not, the module may use the last 4,000 average stress magnitudes to compute a $90^{th}$ percentile average stress magnitude. The module may then determine if the current average stress magnitude exceeds the $90^{th}$ percentile average stress magnitude. If so, the module may intervene with an appropriate intensity based on the effectiveness of recent interventions.

BRIEF DESCRIPTION OF THE SEVERAL VIEWS OF THE DRAWING

While the specification concludes with claims particularly pointing out and distinctly claiming the subject matter that is regarded as forming the various embodiments of the present disclosure, it is believed that the invention will be better understood from the following description taken in conjunction with the accompanying figures:

DETAILED DESCRIPTION OF THE INVENTION

Figure 1:
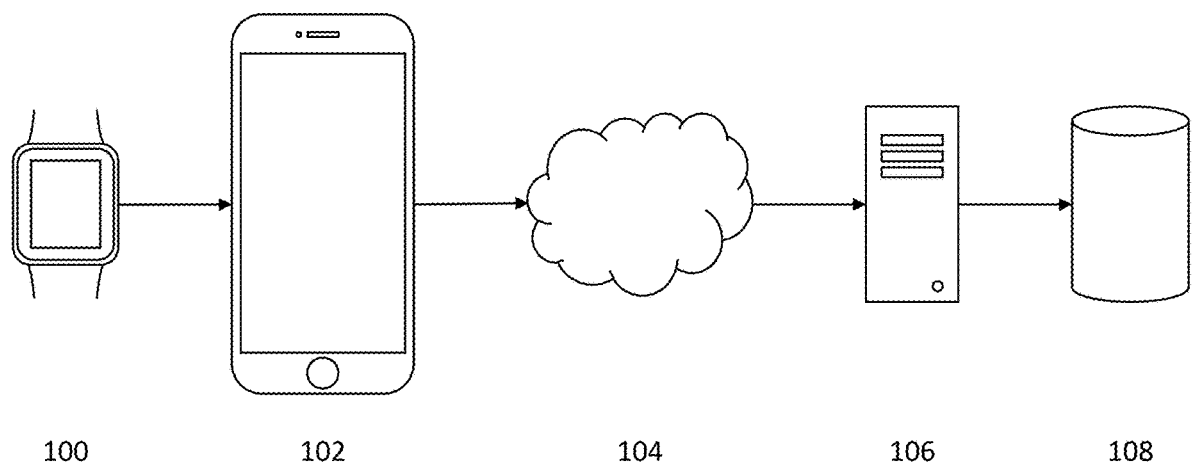
FIG. 1: System Diagram

FIG. 1 is a system diagram illustrating an embodiment of the present disclosure. In it, a watch 100 may connect to a phone 102 via Bluetooth or some other means. The phone 102 may connect via a network 104 to a sever 106. The server 106 may connect to a database 108. The database 108 may contain data collected by the watch 100 and/or phone 102. One skilled in the art will recognize that many other system configurations are possible. For example, instead of running an application on a phone 102 that communicates with a watch 100, one might omit the phone 102 and run the application directly on the watch 100. Also, one might omit the network 102, server 106, and database 108 and run in an offline mode. In addition, one might replace the watch 100 with a variety of other devices capable of monitoring a person during sleep and/or intervening in the event of a nightmare. For example, one might replace the watch with an armband, headband, chest band, bed monitor, patch, etc. To intervene in the event of a nightmare, one might use haptic feedback, lights, sound, etc. In addition, one might combine these devices in a variety of ways.

Figure 2:
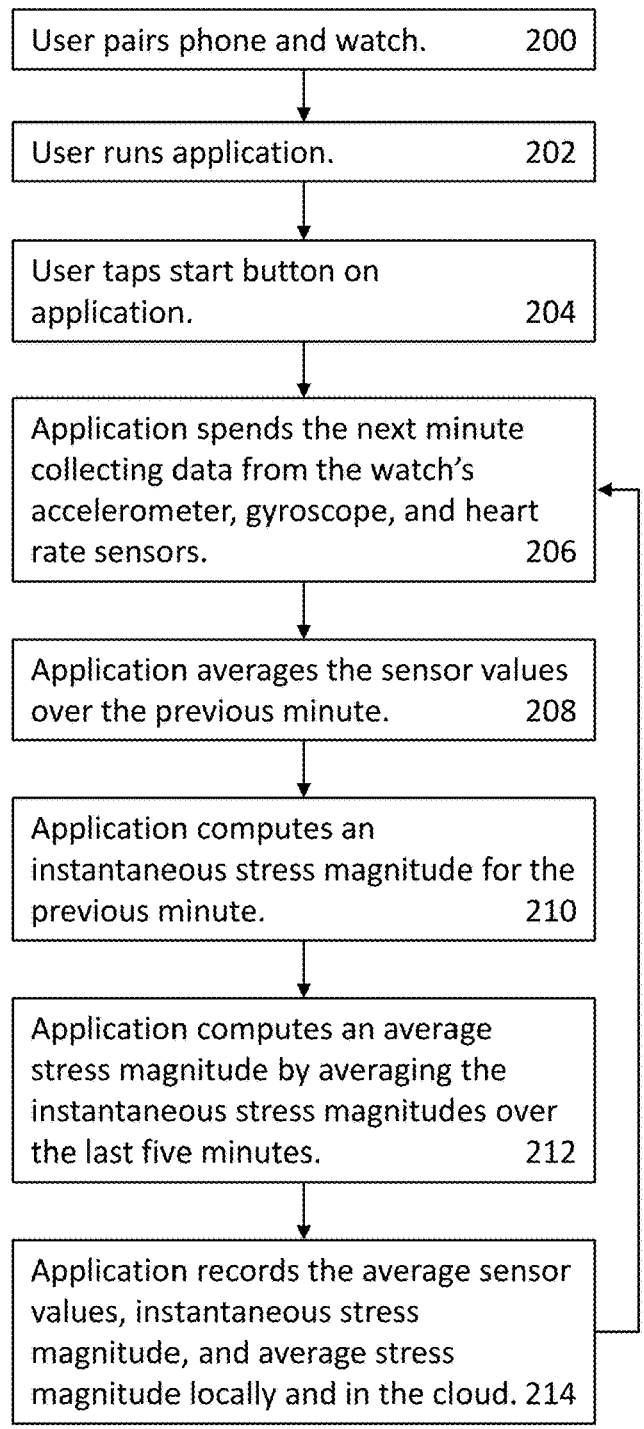
FIG. 2: Monitor Flowchart

FIG. 2 is a monitor flowchart of an embodiment of the present disclosure. In it, a user may begin at step 200 by pairing a phone 102 and watch 100. At step 202, the user may run the application on the phone 102. At step 204, the user may tap a start button in the application. At step 206, the application may spend the next minute collecting data from the watch's accelerometer, gyroscope, and heartrate sensors. At step 208, the application may average the sensor values over the previous minute. At step 210, the application may compute an instantaneous stress magnitude for the previous minute. To do this, one might use the following equations:

$$g = \sqrt{g_x^2 + g_y^2 + g_z^2}$$

$$s = \frac{\sqrt{0.125a^2 + 0.125g^2 + h^2}}{1.6125}$$

The first equation may enable one to compute a gyroscope magnitude from the gyroscope's components. The second equation may enable one to calculate a stress magnitude from accelerometer, gyroscope, and heart rate values. For example, let's say we have an average accelerometer value of 51 meters per second squared, average gyroscope values of (x=40, y=20, and z=185) radians per second, and an average heartrate of 75 beats per minute. The first equation gives us a gyroscope magnitude of approximately 190 radians per second. The second equation gives us a stress magnitude of approximately 63.

$$g = \sqrt{40^2 + 20^2 + 185^2} \approx 190$$

$$s = \frac{\sqrt{0.125(51)^2 + 0.125(190)^2 + (75)^2}}{1.6125} \approx 63$$

At step 212, the application may compute an average stress magnitude by averaging the instantaneous stress magnitudes over the last five minutes. At step 214, the application may record the average sensor values, instantaneous stress magnitude, and average stress magnitude locally and in the cloud.

One skilled in the art will recognized that one could use a variety of sensors to monitor a user including accelerometers, galvanic skin response sensors, gyroscopes, heartrate sensors, oximetry sensors, microphones, temperature sensors, etc.

One skilled in the art will also recognize that one could detect not just traumatic nightmares, but also other events such as daytime anxiety episodes, flashbacks, etc. Also, one might detect not just the event, but precursors thereof.

Figure 3:
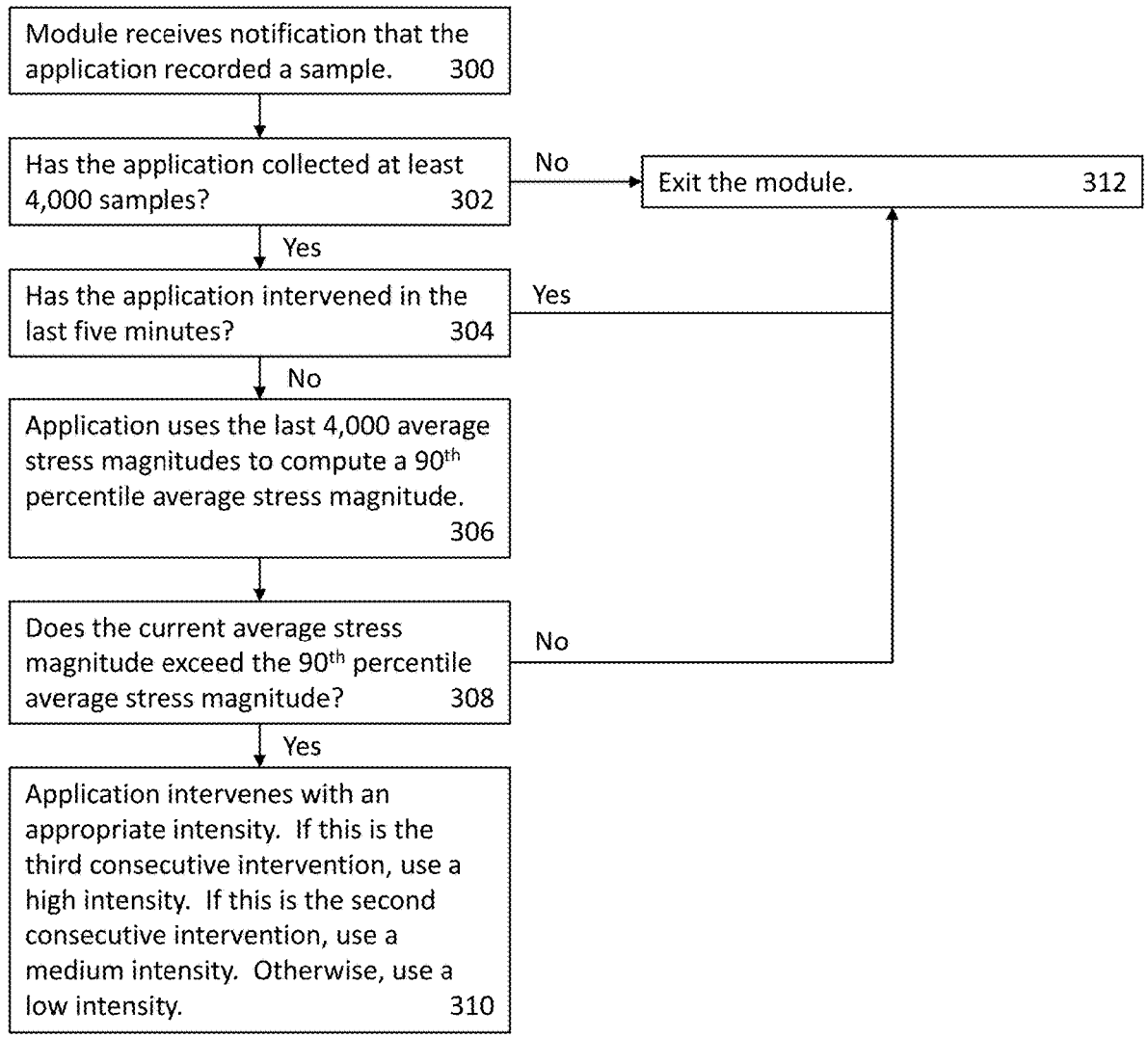
FIG. 3: Intervention Flowchart

FIG. 3 is an intervention flowchart of an embodiment of the present disclosure. At step 300, the module may receive a notification that the application recorded a sample. At step 302, the module may determine whether it has collected at least 4,000 samples. If not, the module may advance to step 312 and exit. If so, the module may advance to step 304 and determine if the module has intervened in the last five minutes. If so, the module may advance to step 312 and exit. If not, the module may advance to step 306 and use the last 4,000 average stress magnitudes to compute a $90^{th}$ percentile average stress magnitude. At step 308, the module may determine if the current average stress magnitude exceeds the $90^{th}$ percentile average stress magnitude. If not, the module may advance to step 312 and exit. If so, the module may advance to step 310 and intervene with an appropriate intensity. If this is the third consecutive intervention, the module may use a high intensity. If this is the second consecutive intervention, the module may use a medium intensity. Otherwise, the module may use a low intensity. One embodiment of the present disclosure uses the following vibration patterns for these intensities. For each pattern, the first number is a duration in millisecond without vibration, the second number is a duration in millisecond with vibration, the third number is a duration in milliseconds without vibration, etc.

Low=0, 150, 100, 150, 500, 150, 100, 150, 500, 150, 100, 150

Medium=0, 250, 100, 250, 500, 250, 100, 250, 500, 250, 100, 250

High=0, 350, 100, 350, 500, 350, 100, 350, 500, 350, 100, 350

In one embodiment of the disclosure, the low intensity intervention may be to arouse, but not awaken. Higher intensity interventions may result in more significant responses including waking the user.

One skilled in the art will recognize that many other equations may be suitable for detecting and responding to a stressful event. One could use different sensors and different equations to detect a stressful event. One could have different training procedures and durations. One could use any number of samples during training. One could use a different percentile to detect a traumatic event or use a different technique to detect these events. One could average results over longer or shorter periods of time. One could use a variety of techniques to intervene (e.g. light or sound). One could use different vibration patterns. One could have any number of different intensity levels. One could have different rules dictating when to intervene. Also, one could easily omit the steps of starting and stopping the monitoring (e.g. there are many techniques to detect sleep states based on biometric indicators).

One skilled in the art will recognize that the application could respond to a detected event in a variety of ways including contacting someone (e.g. via e-mail, phone, or text), scheduling an appointment (e.g. with a doctor or psychiatrist), etc.

One skilled in the art will also recognize that one could simply monitor an individual and not intervene. This may be useful in a variety of settings where one is trying different approaches to address traumatic nightmares and using an embodiment of the present disclosure to see what impact those approaches are having on the individual as he or she sleeps.

Figure 4:
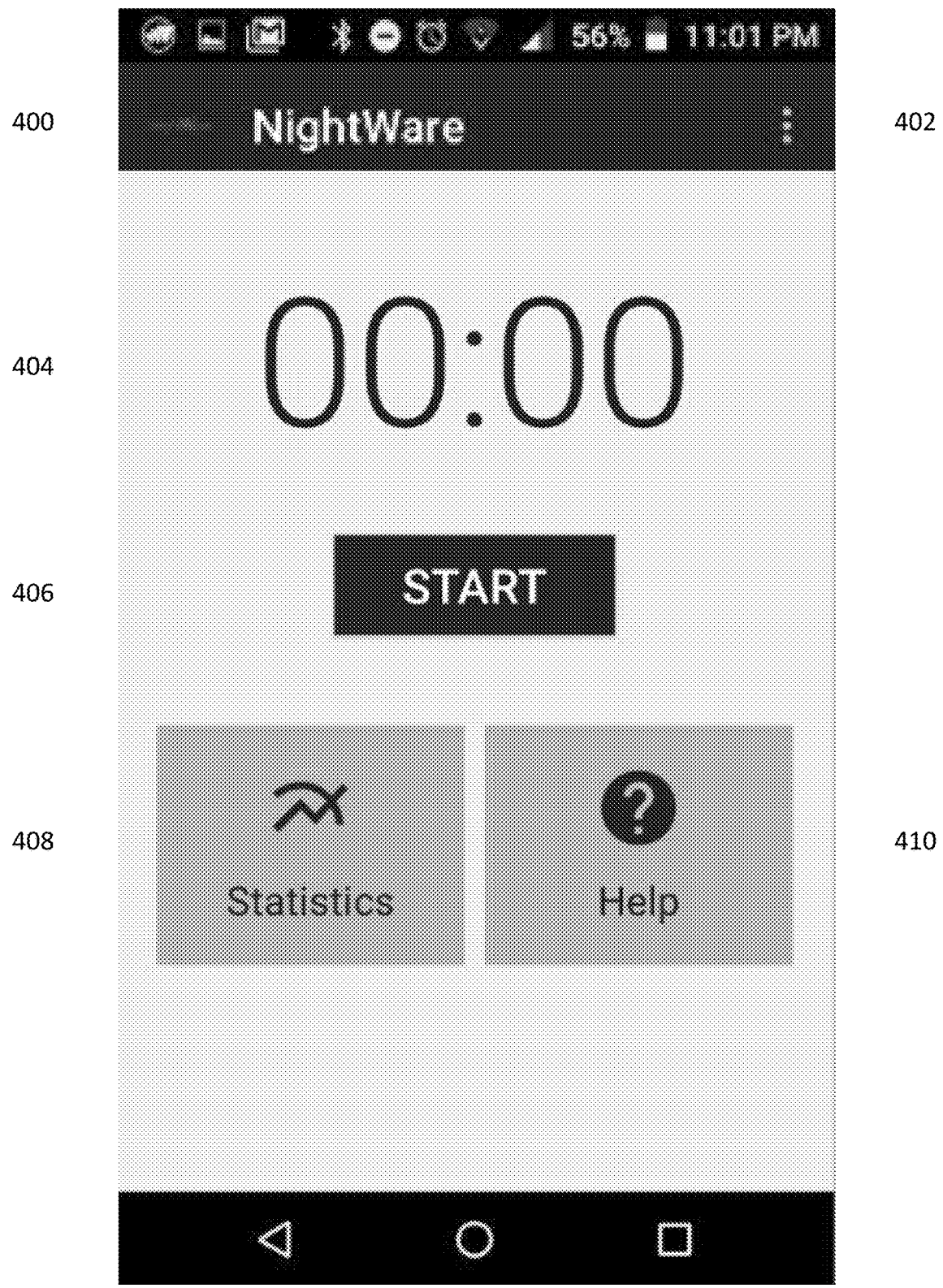
FIG. 4: Start Screen

FIG. 4 is a start screen in an embodiment of the present disclosure. The start screen may enable a user to start monitoring before going to bed. The start screen may include a title 400, menu 402, duration 404, start button 406, statistics button 408, and help button 410. When a user taps the start button 406, the application may show a stop screen (FIG. 5), start monitoring, and start updating the duration 404. When the user taps the statistics button 408, the application may display a statistics screen (FIG. 6).

Figure 5:
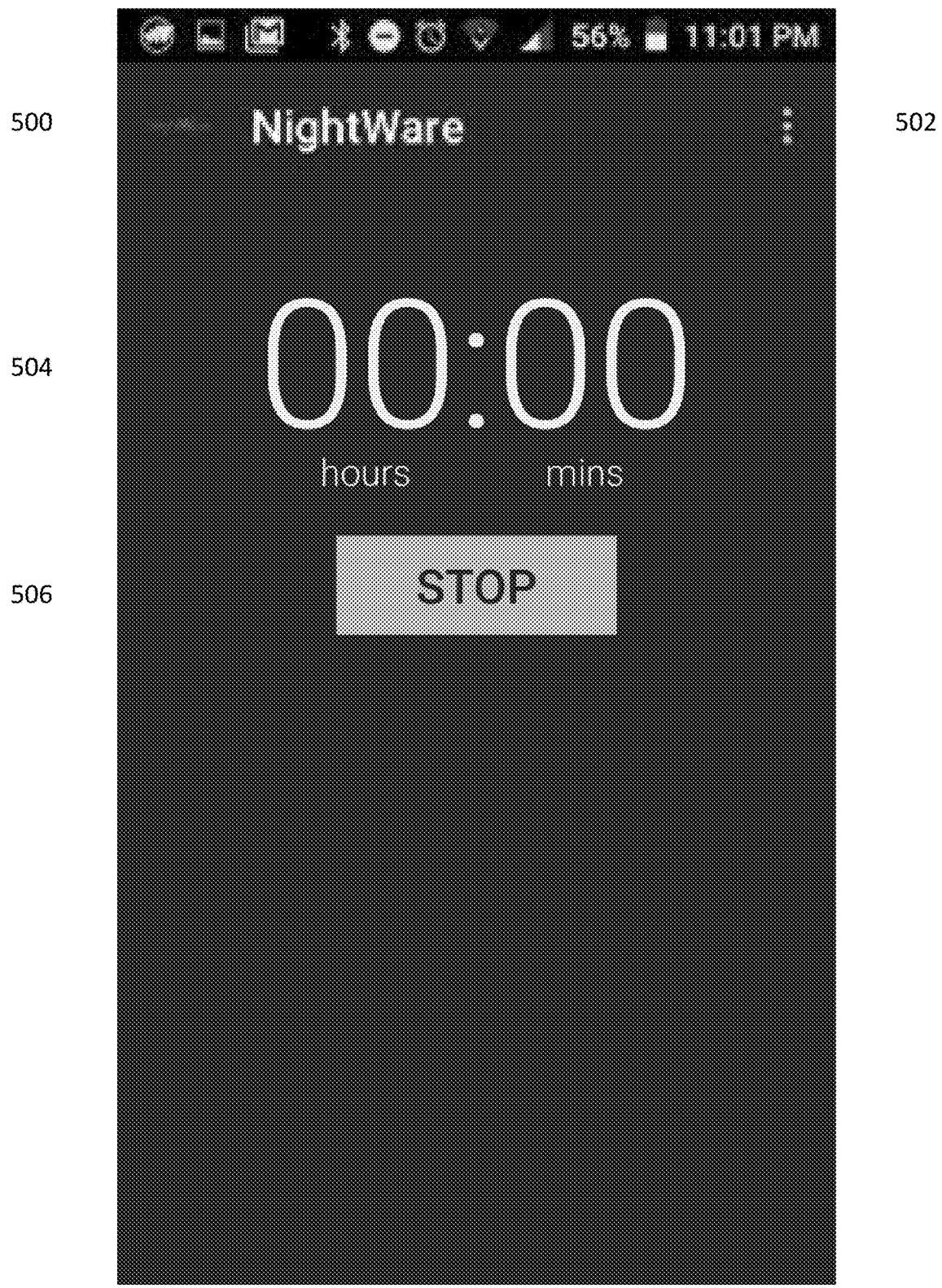
FIG. 5: Stop Screen

FIG. 5 is a stop screen in an embodiment of the present disclosure. The stop screen may enable a user to stop monitoring after waking up. The stop screen may include a title 500, menu 502, duration 504, and stop button 506.

When the user taps the stop button 506, the application may show a start screen (FIG. 4), stop monitoring, and stop updating the duration 504.

Figure 6:
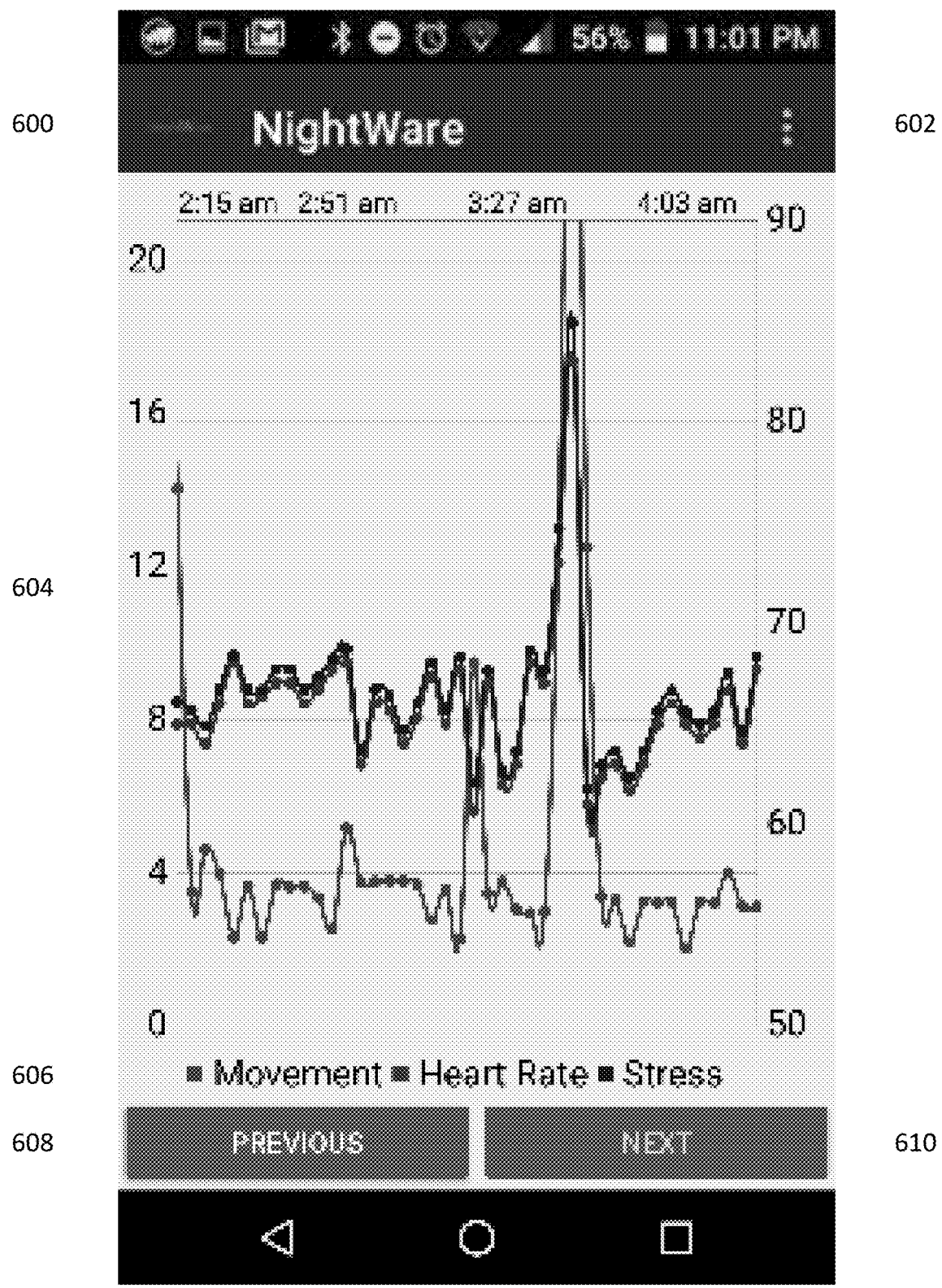
FIG. 6: Statistics Screen

FIG. 6 is a statistics screen in an embodiment of the present disclosure. The statistics screen may enable a user to review heartrate, movement, stress levels during previous nights. The statistics screen may include a title 600, menu 602, chart 604, key 606, previous button 608, and next button 610. The chart 604 may show heartrate, movement, stress levels over time. Tapping the previous button 608 may go back in time and tapping the next button 610 may go forward in time.

We claim:

1. A method of detecting and intervening in stress events of a user, the method comprising:
   collecting training data from at least one monitoring sensor of a device worn by a user, determining training stress magnitudes from the training data, and determining a stress level threshold for the user based on a specified percentile of the training stress magnitudes;
   collecting sample data from the at least one monitoring sensor of the device worn by the user;
   determining a stress magnitude for the user for each of a plurality of first periods of time based on the sample data;
   averaging the stress magnitudes determined for the user over a second period of time that includes the plurality of first periods of time to determine an average stress magnitude for the user;
   comparing the average stress magnitude to the stress level threshold; and
   causing the device worn by the user to generate an intervention when the average stress magnitude exceeds the stress level threshold.

2. The method of claim 1, wherein the training data comprises at least 4,000 sample readings from the at least one monitoring sensor.

3. The method of claim 1, wherein the specified percentile is a $90^{th}$ percentile.

4. The method of claim 1, wherein causing the device worn by the user to generate the intervention comprises causing the device worn by the user to generate the intervention only when both the average stress magnitude exceeds the stress level threshold and there has been at least a specified amount of time since a most recent intervention.

5. The method of claim 4, wherein the specified amount of time is five minutes.

6. The method of claim 1, wherein the at least one monitoring sensor comprises at least one of an accelerometer, a gyroscope, or a heartrate sensor.

7. The method of claim 6, wherein the device worn by the user comprises at least one of a mobile phone and a watch.

8. The method of claim 7, wherein causing the device worn by the user to generate an intervention comprises causing the at least one of the mobile phone and watch to generate at least one of vibration, light, or sound.

9. The method of claim 1, wherein the plurality of first periods of time are each about one minute, and the second period of time is about five minutes.

10. The method of claim 1, wherein an intensity of the intervention is configured to arouse, but not awaken, the user.

11. The method of claim 1, wherein an intensity of the intervention is configured to awaken the user.

12. A system for detecting and intervening in stress events of a user, the system comprising:
    at least one wearable device configured to be worn by a user;
    an application executed at least partially on the at least one wearable device and configured to:
      collect training data from the at least one wearable device, determine training stress magnitudes from the training data, and determine a stress level threshold for the user based on a specified percentile of the training stress magnitudes;
      collect sample data from the at least one wearable device;
      determine a stress magnitude for each of a plurality of first periods of time based on the sample data;
      average the determined stress magnitudes over a second period of time that includes the plurality of first periods of time to determine an average stress magnitude;
      compare the average stress magnitude to the stress level threshold; and
      cause the at least one wearable device to generate an intervention when the average stress magnitude exceeds the stress level threshold.

13. The system of claim 12, further comprising a database for storing at least some of the sample data, the stress magnitudes, and the average stress magnitude.

14. The system of claim 12, wherein the at least one wearable device comprises at least one of an accelerometer, a gyroscope, or a heartrate sensor.

15. The system of claim 12, wherein causing the at least one wearable device to generate an intervention comprises causing the at least one wearable device to generate at least one of vibration, light, or sound.

16. The system of claim 12, wherein the training data comprises at least 4,000 sample readings from the at least one wearable device.

17. The system of claim 12, wherein the specified percentile is a $90^{th}$ percentile.

18. The system of claim 12, wherein causing the at least one wearable device to generate the intervention comprises causing the device worn by the user to generate the intervention only when both the average stress magnitude exceeds the stress level threshold and there has been at least a specified amount of time since a most recent intervention.

19. The system of claim 12, wherein an intensity of the intervention is configured to arouse, but not awaken, the user.

20. The system of claim 12, wherein the plurality of first periods of time are each about one minute, and the second period of time is about five minutes.

* * * * *